United States Patent [19]
Gosselin et al.

[11] Patent Number: 5,627,185
[45] Date of Patent: May 6, 1997

[54] ACYCLOVIR DERIVATIVES AS ANTIVIRAL AGENTS

[76] Inventors: Gilles Gosselin, Rue Paul-Rimbaud, 34000 Montpellier; Jean-Louis Imbach, Place Eugene Bataillon, 34095 Montpellier, both of France

[21] Appl. No.: 465,450

[22] Filed: Jun. 5, 1995

Related U.S. Application Data

[63] Continuation-in-part of Ser. No. 416,515, Apr. 4, 1995, which is a continuation-in-part of Ser. No. 343,433, Nov. 23, 1994, abandoned.

[51] Int. Cl.$^6$ ..................................................... A61K 31/52
[52] U.S. Cl. ........................... 514/269; 514/261; 514/262; 514/885; 514/894; 544/264; 544/265
[58] Field of Search ........................................ 514/261, 262, 514/885, 894, 269; 544/264, 265

[56] References Cited

U.S. PATENT DOCUMENTS

| | | | |
|---|---|---|---|
| 4,294,831 | 10/1981 | Schaffer | 514/261 |
| 4,355,032 | 10/1982 | Verheyden et al. | 514/261 |
| 5,284,837 | 2/1994 | Lindborg et al. | 514/261 |
| 5,494,912 | 2/1996 | Halazy et al. | 514/261 |

FOREIGN PATENT DOCUMENTS

| | | |
|---|---|---|
| 0130126 | 1/1985 | European Pat. Off. ............ 514/261 |
| 0138683 | 4/1985 | European Pat. Off. ............ 514/261 |
| 0217580 | 8/1987 | European Pat. Off. . |
| 0322384 | 6/1989 | European Pat. Off. . |
| 0481214 | 10/1991 | European Pat. Off. . |
| 2654106 | 10/1991 | France . |
| WO90/08155 | 7/1990 | WIPO . |
| WO91/14696 | 3/1991 | WIPO . |
| WO91/19721 | 12/1991 | WIPO . |

OTHER PUBLICATIONS

Hao et al., "2', 3'-Dideoxyuridine Triphosphate: A Potent Inhibitor of HIV Reverse Transcriptase," Proceedings of AACR, vol. 29, p. 348 (1988).

Hao et al., Molecular Pharmacology, vol. 37, pp. 157–163 (1989).

Rosenberg et al., Collection Czech Chem. Commun., vol. 52 pp. 2792–2800. (1987).

Matthes et al., Biochem and Biophysical Research Commun., vol. 148, No. 1, pp. 78–85, (1987).

*Primary Examiner*—James O. Wilson
*Attorney, Agent, or Firm*—Woodcock Washburn Kurtz Mackiewicz & Norris

[57] ABSTRACT

Derivatives of Acyclovir are provided having patent antiviral inhibitory activity. Phosphotriester derviatives are preferred which have the structure:

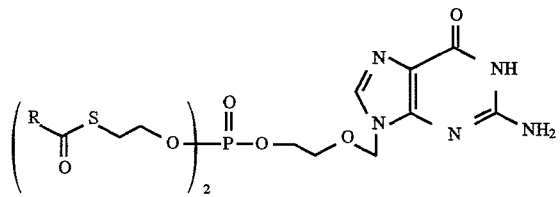

where R is alkyl, especially $CH_3$ or $(CH_3)_3C$.

14 Claims, 1 Drawing Sheet

ACYCLOVIR DERIVATIVES AS ANTIVIRAL AGENTS

CROSS REFERENCE TO PRIOR APPLICATIONS

This application is a continuation in part of Ser. No. 08/416,515 filed Apr. 4, 1995, which is a continuation in part of Ser. No. 08/343,433, filed Nov. 23, 1994, now abandoned, which is related to PCT/FR93/00498 dated May 24, 1993. This application is also related to French patent applications Serial Number 95-04797 filed Apr. 21, 1995, Serial Number 92-06383 filed May 25, 1992 and Serial Number 93-04117 filed Apr. 7, 1993. Each of the foregoing is incorporated herein by reference.

BACKGROUND OF THE INVENTION

This application is directed to phosphotriester derivatives of the drug molecule known as acyclovir (ACV) and their use as antiviral agents.

In prior patent application, PCT/FR93/00498 that published as WO93/24510, a very general approach that allows for intracellular delivery of mononucleotides using nucleosidic phosphotriesters bearing two bioreversible protecting groups was described by the present inventors.

It has now been found that this approach can be used for those nucleoside analogs which, in order to exert their biological activity, need to be phosphorylated into the corresponding triphosphates. Intracellular metabolization, such as phosphorylation, of nucleosides to active nucleotides requires the successive action of three kinases, the first one being highly selective and strongly regulated. As a consequence, if a nucleosidic analog is not phosphorylated by the first kinase, it cannot exert its inhibitory activity.

Some viruses, such as Herpes Simplex virus (HSV), encode for a vital kinase which is able to phosphorylate some nucleoside analogs that are not phosphorylated by cellular kinases. In particular, some acyclonucleosides which are not substrates for the first cellular kinase noted above do not show any activity against viruses which do not provide their own kinase. This is the case for the known antiviral drug, acyclovir (ACV), which has anti-herpetic activity due to its selective monophosphorylation by the thymidine kinase of Herpes Simplex virus. However, acyclovir has no activity against many other viruses, such as Human Immunodeficiency virus (HIV) or Hepatitis B virus (HBV), which do not provide the necessary viral kinases. Moreover, ACV is poorly active against those herpetic viruses in which thymidine kinase activity is either reduced or missing, such as Epstein-Barr virus or Cytomegalovirus. Further, it has been well established that acyclovir resistant Herpes Simplex viruses can appear both in vitro and in vivo, especially in highly immunodepressed patients. This resistance usually arises from a modification of the viral thymidine kinase, which results in a reduction or disappearance of the phosphorylation of ACV.

The intracellular delivery of acyclovir monophosphate (ACVMP) from various kinds of bioreversible phosphotriesters, as described in the patent application PCT/FR93/00498, is thus capable of enlarging the antiviral activity spectrum of this molecule.

In actuality, in comparison with ACV, phosphotriesters of ACV can be considered to be new therapeutic species since their activity spectrum is much larger than of ACV.

It is therefore an object of this invention to provide phosphotriester derivatives of acyclovir together with antiviral pharmaceutical formulations including such compounds.

SUMMARY OF THE INVENTION

Figure 1:
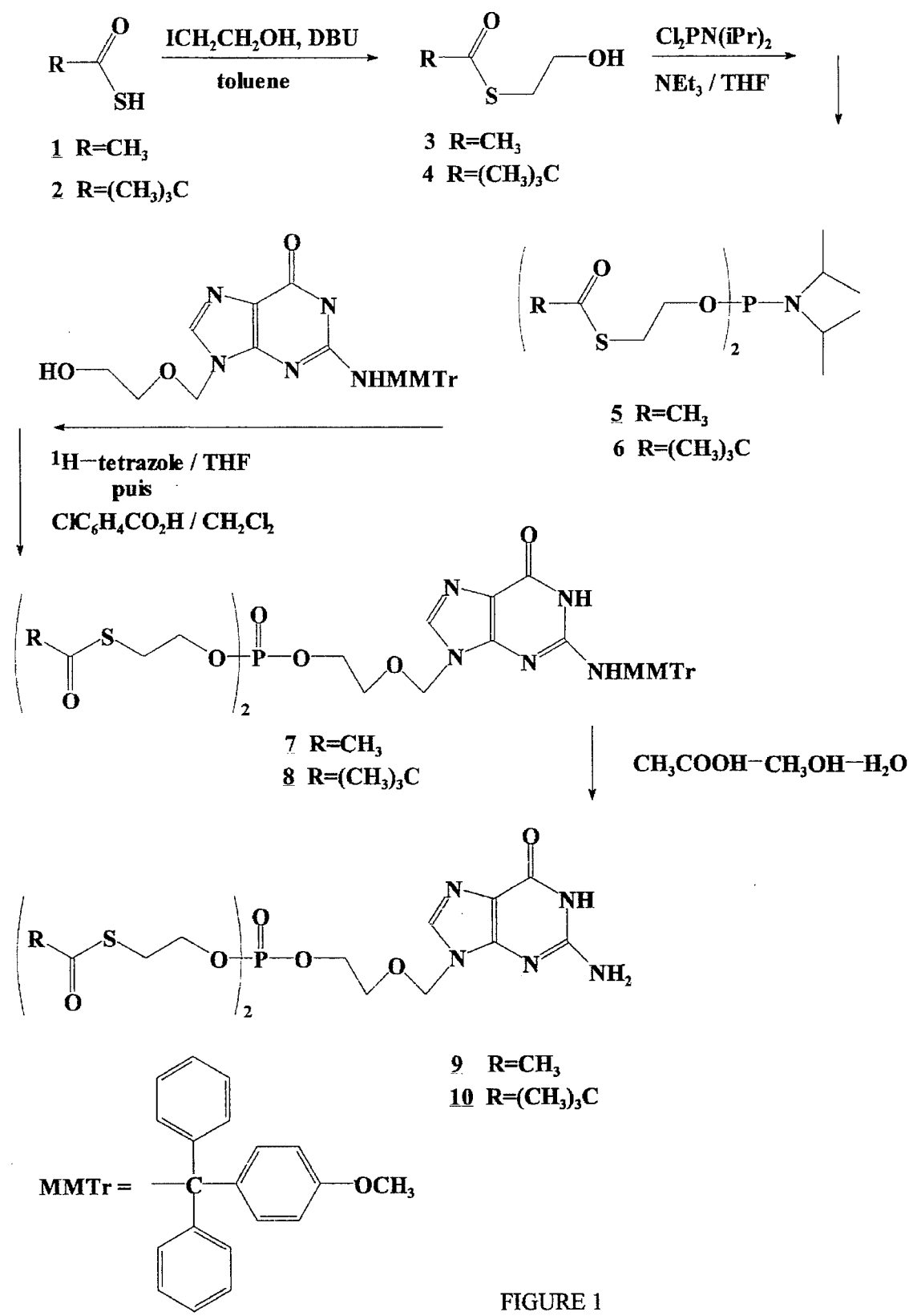
FIG. 1 is an exemplary synthetic scheme for certain, preferred compounds of the invention.

Phosphotriester compounds are provided corresponding to the general formula

I:

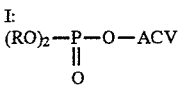

wherein:

R is $—(CH_2)_n—S—X$;

X is

or S—U;

Z is O or S;

Y and U, independently, are alkyl, aryl or a sugar moiety, optionally substituted with OH, SH or $NH_2$;

n is 1 to 4, preferably 1 or 2; and

ACV is an acyclovir moiety having the formula

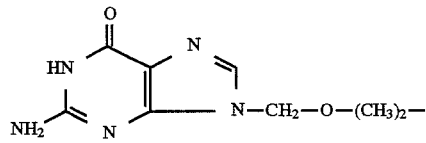

In accordance with the present invention, Y and U are preferably $C_1$ to $C_7$ alkyl; phenyl, benzyl, glucose, mannose, rhamnose, or cyclofuranose. In one embodiment, when X represents SU, U preferably represents the radical $—(CH_2)_{n1}—X^1$ where $X^1$ represents H, OH, SH or $NH_2$ and $n^1$ is equal to 1 to 4, preferably 1 or 2.

There are especially mentioned the compounds (I) for which R represents $—(CH_2)_2—S—S—(CH_2)_2—OH$. In a preferred embodiment, X is

and Y is $CH_3$ or tertiary butyl (tbu).

There are especially mentioned the compounds (I) for which R represents $(CH_2)_n—S—C(=O)—CH_3$ or $(CH_2)_n—S—C(=O)—tBU$ with n=1 or 2.

Also preferred are compounds of formula (Ia):

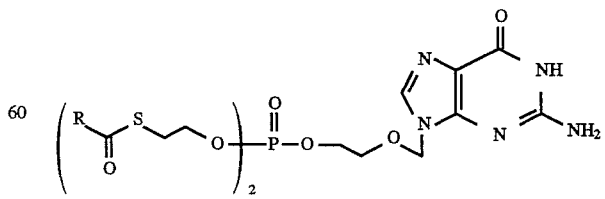

where R is alkyl, especially $CH_3$ or $(CH_3)_3C$.

In general, the compounds according to the invention are prepared utilizing processes known to those skilled in the art. Such processes are described in published patent application PCT/FR93/00498, published as WO 93/24510. In preparing compounds of the invention, the functional groups such as R and, optionally, the group ACV can be protected by suitable protecting groups, followed by deprotection of the said functional groups such as R, and possibly ACV, to give compounds of formula (I).

For example, a compound of formula (II):

II:

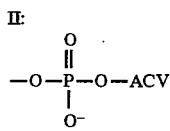

where ACV, which can optionally be derivatized or protected, is reacted with the compound of formula (III), X—S—(CH$_2$)$_n$—OH, where X represents the radical: —C(=Z)—Y or S—U, wherein Z is O or S and Y and U are alkyl, aryl or saccharide radicals that may be optionally substituted, in particular with an OH, SH or NH2 groups, suitably protected, in order to obtain the compound of formula (I) in a protected form that can then be deprotected.

In another embodiment, acyclovir is reacted with a phosphitylating reagent followed by an oxidation reaction and, finally deprotection, in order to obtain a compound of formula (I).

This exemplary preparative process is illustrated in the following detailed description, in which other characteristics and advantages of the present invention also appear.

The compounds of the invention can be included in antiviral pharmaceutical compositions that include a phosphotriester compound of the invention as an active substance together with a pharmaceutically acceptable diluent excipient or carrier.

The invention is further directed to antiviral compositions as for example anti-HBV anti-HIV, and anti-CMV (cytomegalovirus) compositions together with other antiviral compositions directed against other viruses in which thymidine kinase activity is either reduced or missing. The present invention also provides anti-HSV compositions of increased therapeutic activity.

Other characteristics and advantages of the invention will be evident from review of the detailed examples and descriptions that follow.

Compounds of formula (Ia) can be prepared in which the bioreversible protection, a substrate for cellular carboxyesterases, is an S-acyl thioalkyl group. Acyclovir (preferably, suitably protected at position 2) is coupled with an appropriate phosphitylating reagent. Deprotection yields compounds of formula Ia in which the R group can be, variously, alkyl, aryl, heterocycle, sugar, and the like.

I. SYNTHESIS

A. General Conditions

Thin layer chromatography was performed on Merck 60F 254 silica plates (Art. 5554). Column chromatography on silica gel were carried out with Merck 60 H silica (Art. 7719) or with RP2 Merck silanized silica (Art. 7719).

Before analysis or lyophilization, solutions were filtered on Millex HV-4 filter (Millipore).

UV spectra were recorded on a UVIKON 810 spectrophotometer.

Mass spectra were taken on a JEOL JMS DX 300 apparatus by the FAB ionization method in positive or negative mode in a matrix of glycerol (G), glycerol/thioglycerol (GT) or 3-nitrobenzyl alcohol (NBA).

Proton NMR spectra were recorded on a Varian EM 360 apparatus or on a Bruker AC 250 apparatus. The chemical shifts are expressed in ppm relative to the tetramethylsilane (TMS) signal. The multiplicity and the appearance of the signals observed by NMR are indicated by one or more letter(s): s(singlet), d(doublet), t(triplet), m(multiplet), or b (broad). Phosphorus NMR spectra were recorded on a Bruker WP 200 SY apparatus with proton decoupling. The chemical shifts are expressed in ppm relative to the H$_3$PO$_4$ signal, which is taken as the external reference.

B. Synthetic Scheme

Figure I depicts an exemplary synthetic scheme for preparing certain compositions in accordance with the invention. bis-acetyl thiosorer, BIS(SATE) and bis-S-pivaloyl thioethyl, BIS(SPTE) phosphotriester derivatives of acyclovir are shown. These correspond to formula Ia where R=CH$_3$ and R=(CH$_3$)$_3$C.

EXAMPLE 1

2,2-Dimethylthiopropanoic acid 2

Hydrogen sulfide was bubbled with stirring for 1½ hours into anhydrous pyridine (200 ml) maintained at −30° C. Pivaloyl chloride (62 ml, 0.5 mol) was added dropwise to the resulting solution over 1 hour while maintaining the reaction mixture at −30° C. A 5N solution of sulfuric acid (425 ml) was slowly added in order to obtain a pH close to 5. The two layers were separated, and the organic layer was diluted with ether, dried over sodium sulfate, filtered and concentrated under reduced pressure. The residue was then evaporated under reduced pressure to afford compound 2 (47 g, 80%).

$^1$H NMR (CDCL$_3$), δ: 3.69 (s1, 1H, SH); 1.27 (s, 9H, (CH$_3$)$_3$). Mass spectra, (matrix=NBA), FAB neg., 117 (M—H). Boiling point: 64° C. (92 mm Hg).

EXAMPLE 2

S-Acetylthioethanol or S-2-hydroxyethylthioacetate 3

1,8-Diazabicyclo-(5,4,0)undec-7-ene (DBU) (33.7 ml, 0.23 mol) and iodoethanol (15.6 ml, 0.20 mol) were consecutively added at 0° C. to a stirred solution of commercial thioacetic acid (16.5 ml, 0.23 mol) in toluene (80 ml). The reaction mixture was allowed to react for two hours at room temperature, then diluted with methylene chloride and washed with water. The organic layer was dried over sodium sulfate, filtered and concentrated under reduced pressure. The crude residue 3, (15.3 g, 64%), was used in the following condensation step without further purification.

$^1$H NMR (DMSO-d$_6$), δ: 4.95 (t, 1H, CH$_2$OH, J=5.5 Hz); 3.45 (m, 2H, CH$_2$CH$_2$OH); 2.90 (t, 2H, SCH$_2$CH$_2$, J=6.6 Hz); 2.31 (s, 3H, CH$_3$).

EXAMPLE 3

S-pivaloylthioethanol or S-(2,2-dimethylpropanoyl) thioethanol or S-2-hydroxyethylthio(2,2-dimethyl) propionate 4

1,8-Diazabicyclo-(5,4,0)undec-7-ene (DBU) (4.2 ml, 29 mmol) and iodoethanol (1.95 ml, 25 mmol) were consecutive added at 0° C. to a stirred solution of 2,2-dimethylpropanoic acid 2 (3.43 g, 29 mmol) in toluene (12 ml). The reaction mixture was allowed to stand two hours at room temperature, then diluted with methylene chloride and washed with water. The organic layer was dried over sodium sulfate, filtered and concentrated under reduced pressure. The crude residue was dissolved in a small amount of methylene chloride and chromatographed on a silica gel column using a stepwise gradient of methanol (0–2%) in methylene chloride to give the title compound 4 (3.6 g, 89%).

$^1$H NMR (DMSO-d$_6$), δ: 4.94 (t, 1H, CH$_2$O$\underline{H}$, J=5.5 Hz); 3.45 (m, 2H, CH$_2$C$\underline{H}_2$OH); 2.88 (t, 2H, SC$\underline{H}_2$CH$_2$, J=6.6 Hz); 1.16 (s, 9H, (CH$_3$)$_3$)C).

EXAMPLE 4

O,O'-Bis(S -acetylthioethyl)N,N-diisopropylphosphoramidite 5

A solution of S-acetyl thioethanol 3 (4.81 g, 40 mmol) and triethylamine (6.1 ml, 44 mmol) in THF (100 ml), cooled at –78° C., was added over a period of 45 minutes to a solution of N,N-diisopropylphosphorodichloridite (4.04 g, 20 mmol) in THF (150 ml). The reaction mixture was allowed to stand for two hours at room temperature, then filtered and evaporated under reduced pressure. The residue was dissolved in cyclohexane, filtered and evaporated under reduced pressure. The resulting pale yellow colored oil was dissolved in a small amount of cyclohexane containing 1% of triethylamine and chromatographed on a silica gel column that contained cyclohexane having 5% triethylamine. The column was eluted with ethylacetate (0–2%) in cyclohexane containing 1% triethylamine to yield the title compound, 5 (5.3 g, 72%).

$^1$H NMR (DMSO-d$_6$), δ: 3.59 (m, 6H, CH$_2$O$\underline{H}$ or C$\underline{H}$); 3.04 (t, 4H, SC $\underline{H}_2$CH$_2$, J=6.4 Hz); 2.32 (s, 6H, CH$_3$CO); 1.10 (d, 12H, (C$\underline{H}_3$)$_2$CH, J=6.8 Hz); $^{31}$P NMR (DMSO-d$_6$), δ: 147.9. Mass spectra (matrix GT), FAB pos.: 370 (M+H)$^+$; 103 (CH$_3$COSCH$_2$CH$_2$)$^+$.

EXAMPLE 5

O,O-Bis(S-(2,2-dimethylpropanoyl)thioethyl)N,N-diisopropylphosphoramidite 6

A solution of S-(2,2-dimethylpropanoyl)thioethanol 4 (5 g, 30.6 mmol) and triethylamine (4.7 ml, 33.7 mmol) in THF (60 ml) cooled at –78° C., is added over a period of 15 minutes to a solution of N,N-diisopropylphosphorodichloridite (3.09 g, 15.3 mmol) in THF (130 ml). The reaction mixture was allowed to stand for two hours at room temperature, then filtered and evaporated under reduced pressure. The residue was dissolved in cyclohexane, filtered and evaporated under reduced pressure. The resulting pale-yellow colored oil was dissolved in a small amount of cyclohexane containing 1% of triethylamine, and chromatographed on a silica gel column containing cyclohexane having 5% of triethylamine. The column was eluted with ethylacetate (0–2%) in cyclohexane containing 1% of triethylamine to yield the title compound 6 (3.2 g, 46%).

$^1$H NMR (DMSO-d$_6$), δ: 3.59 (m, 6H, CH$_2$O$\underline{H}$ or C$\underline{H}$); 3.01 (t, 4H, SC $\underline{H}_2$CH$_2$, J=6.3 Hz); 1.16 (s, 18H, (CH$_3$)$_3$C); 1.10 (d, 12H, (C$\underline{H}_3$)$_2$CH, J=6.8 Hz); $^{31}$P NMR (DMSO-d$_6$), δ: 148.0. Mass spectra (matrix GT), FAB pos.: 454 (M+H)$^+$; 145 ((CH$_3$)$_3$CCOSCH$_2$CH$_2$)$^+$; 85 ((CH$_3$)$_3$CCO)$^+$; 57 ((CH$_3$)$_3$C)$^+$.

EXAMPLE 6

O-[1-(Methyl-(9-(N$^2$-p-anisyldiphenylmethyl) guanin-yl))1-hydroxyethyl-2-yl]-O',O"-bis(S-acetyl-2-thioethyl)phosphate 7

Tetrazole (210 mg, 3.0 mmol) was added to a stirred solution of N$^2$-(p-anisyldiphenylmethyl)-9-[(-2-hydroxyethoxy)methyl] guanine prepared in accordance with Martin et al., *J. Med. Chem.*, 1986, 29, 1384–1386 (500 mg, 1.0 mmol) and reagent 5 (445 mg, 1.2 mmol) in THF (3.0 ml). After 35 min at room temperature, the reaction mixture was cooled to –40° C. and a solution of 3-chloroperbenzoic acid (407 mg, 1.3 mmol) in methylene chloride (5 ml) was added. The solution was then allowed to return at room temperature over one hour. Sodium hydrogen sulfite (10% solution, 3 ml) was added to reduce the excess of the peracid. The organic layer was separated, diluted with methylene chloride (10 ml), washed with a saturated aqueous solution of sodium bicarbonate (3 ml), then with water (3×3 ml), dried over Na$_2$SO$_4$ and evaporated to dryness. The residue was dissolved in a small amount of methylene chloride and chromatographed on a silica gel column (methanol (0–4%) in methylene chloride). Compound 7 was obtained as a white foam (531 mg, 68%).

$^1$H NMR (DMSO-d$_6$), δ: 10.63 (s, 1H, NH); 7.71 (s, 1H, NH); 7.67 (s, 1H, H-8); 7.16–7.31 (m, 12H, aromatic); 6.87 (d, 2H, aromatic, J=8.9 Hz); 4.86 (s, 2H, NCH$_2$O); 3.97 (m, 4H, OC$\underline{H}_2$CH$_2$S); 3.71 (sl, 5H, OCH$_3$ or POC$\underline{H}_2$CH$_2$O); 3.10 (t, 4H, OCH$_2$C$\underline{H}_2$S, J=6.3 Hz); 3.03 (m, 2H, POCH$_2$, C$\underline{H}_2$O); 2.35 (s, 6H, CH$_3$COS); $^{31}$P NMR (DMSO-d$_6$): δ –0.83. Mass spectra (matrix GT), FAB pos.: 782 (M+M)$^+$; 273 (trityl)$^+$; 103 (CH$_3$COSCH$_2$CH$_2$)$^+$; FAB neg.: 780 (M—H)$^-$; 678 (M—CH$_3$COSCH$_2$CH$_2$)$^-$.

EXAMPLE 7

O-[1-(Methyl-[9-(N$^2$-p-anisyldiphenylmethyl) guanin-yl])1-hydroxyethyl-2-yl]-O',O"-bis(S-pivaloyl-2thioethyl) phosphate 8

Tetrazole (126 mg, 1.8 mmol) was added to a stirred solution of N$^2$-(p-anisyldiphenylmethyl)-9-[(-2-hydroxyethoxy)methyl] guanine prepared in accordance with Martin et al., *J. Med. Chem.*, 1986, 29, 1384–1386 (300 mg, 0.60 mmol) and compound 6 (408 mg, 0.90 mmol) in THF (1.8 ml). After 35 min at room temperature, the reaction mixture was cooled to –40° C. and a solution of 3-chloroperbenzoic acid (342 mg, 0.99 mmol) in methylene chloride (4 ml) was added. The solution was then allowed to warm to room temperature over one hour. Sodium hydrogensulfite (10% solution, 3 ml) was added in order to reduce the excess of peracid. The organic layer was separated, diluted with methylene chloride (10 ml), washed with a saturated aqueous solution of sodium bicarbonate (3 ml), then with water (3×3 ml), dried over Na$_2$SO4 and evaporated to dryness. The residue was dissolved in a small amount of methylene chloride and chromatographed on a silica gel column (methanol (0–4%) in methylene chloride) to give compound 8 as a white foam (372 mg, 71%).

$^1$H NMR (DMSO-d$_6$), δ: 10.63 (s, 1H, NH); 7.71 (s, 1H, NH); 7.68 (s, 1H, H-8); 7.17–7.30 (m, 12H, aromatic); 6.86 (d, 2H, aromatic, J=8.9 Hz); 4.87 (s, 2H, NCH$_2$O); 3.97 (m, 4H, OC$\underline{H}_2$CH$_2$S); 3.71 (sl, 5H, OCH$_3$ or POC$\underline{H}_2$CH$_2$O); 3.09 (t, 4H, OCH$_2$C$\underline{H}_2$S, J=6.4 Hz); 3.06 (m, 2H, POCH$_2$, C$\underline{H}_2$O); 1.17 (s, 18H, (CH$_3$)$_3$C); amp NMR (DMSO-d$_6$) δ: –0.88. Mass spectra (matrix GT), FAB pos.: 866 (M+M)$^+$; 273 (trityl)$^+$; 145 ((CH$_3$)$_3$CCOS$\underline{H}$C$_2$CH$_2$)$^+$; FAB neg.: 864 (M—H)$^-$; 720 (M—(CH$_3$) $_3$CCOSCH$_2$CH$_2$)$^-$.

EXAMPLE 8

O-[1-(Methyl-[9-guanin-yl])-1-hydroxyethyl-2-yl]-O',O"-bis(S-acetyl-2-thioethyl) phosphate 9 (Bis [SATE]ACVMP)

A solution of compound 7 (450 mg, 0.57 mmol) in a mixture of acetic acid (32 ml), methanol (4 ml) and water (4 ml) was heated at 50° C. for 18 hours, then evaporated to dryness. The residue was coevaporated three times with ethanol, then twice with methylene chloride, then diluted in a small amount of methylene chloride and chromatographed on a silica gel column (methanol (0–10%) in methylene chloride). The desired compound 9 was obtained as a white foam (270 mg, 92%).

UV: λ max (EtOH 95) 253 nm (ε 14100). $^{1}$H NMR (DMSO-d$_6$): δ 10.65 (s, 1H, NH); 7.81 (s, 1H, H-8); 6.52 (s, 2H, NH$_2$); 5.35 (s, 2H, NCH$_2$O); 4.05 (m, 2H, POC$\underline{H}_2$CH$_2$O); 3.99 (m 4H, OC$\underline{H}_2$CH$_2$S); 3.65 m, 2H, POCH$_2$, C$\underline{H}_2$O); 3.09 (t, 4H, OCH$_2$C$\underline{H}_2$S, J=6.3 Hz); 2.34 (s, 6H, CH$_2$COS); $^{31}$P NMR (DMSO-d$_6$): δ −0.74. Mass spectra (matrix GT), FAB pos.: 510 (M+M)$^+$; 152 (BH$_2$)$^+$; 103 (CH$_3$COSCH$_2$CH$_2$)$^+$; FAB neg.: 508 (M—H)$^-$; 406 (M—(CH$_3$COSCH$_2$CH$_2$)$^-$; 150 (B)$^-$.

EXAMPLE 9

O-[1-(Methyl-[9-guanin-yl]) -1-hydroxyethyl-2-yl]-O',O''-bis(S-pivaloyl-2 -thioethyl) phosphate 10 (Bis [SPTE]ACVMP)

A solution of compound 8 (360 mg, 0.42 mmol) in a mixture of acetic acid (24 ml), methanol (3 ml) and water (3 ml) was heated at 50° C. for 18 hours, then evaporated to dryness. The residue was coevaporated three times with ethanol, then twice with methylene chloride, then diluted in a small amount of methylene chloride and chromatographed on a silica gel column (methanol (0–9%) in methylene chloride). The desired compound 10 was obtained as a white foam (210 mg, 85%).

UV: λ max (EtOH 95) 253 nm (ε 13400). $^{1}$H NMR (DMSO-d$_6$): δ 10.59 (s, 1H, NH); 7.79 (s, 1H, H-8); 6.46 (s, 2H, NH2); 5.36 (s, 2H, NCH$_2$O); 3.95–4.09 (m, 6H, POCH$_2$CH$_2$O or OCH$_2$CH$_2$S); 3.67 (m, 2H, POCH$_2$C$\underline{H}_2$O); 3.08 (t, 4H, OCH$_2$C$\underline{H}_2$S, J=6.3 Hz); 1.17 (s, 18H, (CH$_3$)$_3$C); $^{31}$P NMR (DMSO-d$_6$): δ −0.80. Mass spectra (matrix GT), FAB pos.: 594 (M+H)$^+$; 152 (BH$_2$)$^+$; 145 ((CH$_3$)$_3$CCOSCH$_2$CH$_2$)$^+$; FAB neg.: 592 (M—H)$^-$; 448 (M—(CH$_3$)$_3$CCOSCH$_2$CH$_2$)$^-$; 150 (B)$^-$.

II. BIOLOGICAL EVALUATIONS

The experimental procedure used for evaluation of activity against Hepatitis B virus is as previously described by Korba and Milman in Antiviral Res. 217, 217 (1991).

The experimental procedure used for evaluation of activities against Human Immunodeficiency virus (HIV) is as follows:

HIV-1 replication (LAI isolate) in CEM cells are measured by assaying for transcriptase (RTase) in the culture supernatant after infection for five days. This activity reflects the presence of the virus released by the cells. After absorption of the virus, the test compounds are added at various concentrations in the culture medium. Antiviral activity is expressed as the lowest concentration of compound which reduces the vital production by at least 50% (ED$_{50}$)

The toxic effect on non-infected CEMs is assessed by a calorimetric reaction based on the capacity of living cells to reduce 3-(4,5 dimethylthiazol-2-yl)-2,5 diphenyltetrazolium bromide into formazan after incubation for five days in the presence of various concentrations of the compounds. The results are expressed as the lowest concentration of compound which results in at least 50% inhibition of the formation of formazan (CD$_{50}$).

The experimental procedure used for evaluation of activities against Herpes simplex virus type 1 (HSV-1) is the as described by Genu-Dellac et al. in Nucleosides and Nucleotides, 10, 1345, (1991).

1. Anti-HBV activity on transfected HepG2 (2.2.15) cells of Bis(S-acyl-2-thioethyl)phosphotriester derivatives of Acyclovir, (compound 9 of Figure I), as compared with those of the parent nucleoside and of 2',3'-dideoxyguanosine (ddG) and 2',3'-dideoxycytidine (ddC) are shown in Table 1.

TABLE 1

| Composition | HBV virion | | | |
|---|---|---|---|---|
| | EC$_{50}$(μM) | EC$_{90}$(μM) | CC$_{50}$(μM) | SI |
| ddC | 1.3 ± 0.2 | 1.1 ± 1.2 | 219 ± 19 | 20 |
| ddC | 2.2 ± 0.3 | 8.3 ± 0.8 | 218 ± 19 | 30 |
| Bis(SATE)ACVMP 9 | 0.7 ± 0.1 | 5.1 ± 1 | 987 ± 99 | 194 |
| Bis(SPTE)ACVMP 10 | 0.2 ± 0.04 | 7.1 ± 0.8 | 1593 ± 131 | 224 |
| Acyclovir | 111 ± 15 | >100 | 631 ± 40 | ND |

SI = CC50/EC90; ND = Not Determinable

In Table 1, EC$_{90}$ and EC$_{50}$ represent the molar concentrations which provide respectively a 90% and a 50% inhibition of HBV replication. CC$_{50}$ represents the molar concentration which reduces the viability of non-infected cells by 50%. The data show that both Acyclovir derivatives significantly inhibit HBV activity.

2. Anti-HIV activity on CEM TK- cells of Bis(S-acyl-2-thioethyl) phosphotriesters derivatives of acyclovir, as compared with those of the parent nucleoside and of AZT are shown in Table 2.

TABLE 2

| Composition | EC$_{50}$(μM) | CC$_{50}$μM) |
|---|---|---|
| AZT | >100(20%) | >100(5%) |
| Bis(SATE)ACVMP | 77 | >100(0%) |
| Bis(SPTE)ACVMP | 3.6 | >10(26%) |
| Acyclovir | >100(0%) | >100(0%) |

In Table 2, EC$_{50}$ represents the molar concentration which produces a 50% inhibition of HIV replication. Significant inhibition is shown.

3. Anti HSV activity on MRC-5 cells of Bis(S-acyl-2thioethyl)phosphotriesters derivatives of acyclovir is compared to that of Acyclovir in Table 3.

TABLE 3

| Composition | HSV-1 EC$_{50}$(μM) | HSV-1 TK- EC$_{50}$(μM) |
|---|---|---|
| Bis(SATE)ACVMP | 1.25 | 100 |
| Bis(SPTE)ACVMP | 2.5 | 10 |
| Acyclovir | 0.63 | >100 |

EC$_{50}$ represents the molar concentration which produces a 50% inhibition of HSV-1 replication. Significant activity is shown.

What is claimed:

1. A phosphotriester compound of the structure:

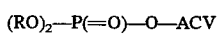

(RO)$_2$—P(=O)—O—ACV where:

R is —(CH$_2$)$_n$—S—X wherein:
  X is —C(=Z)—Y or S—U;
  Z is O or S;
  Y and U are alkyl, aryl or a saccharide which is optionally substituted with OH, SH or NH$_2$;

n is equal to 1 to 4; and

ACV is an acyclovir moiety.

2. The compound of claim 1 wherein the acyclovir moiety has the structure

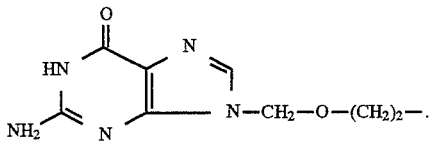

3. The compound of claim 1 wherein X is S—U and U represents the radical $(CH_2)_{n1}$—$X^1$, where $X^1$ is H, OH, SH or $NH_2$, and $n^1$ is 1 to 4.

4. The compound of claim 3 wherein R is —$(CH_2)_2$—S—S—$(CH_2)_2$—OH.

5. A compound having the structure:

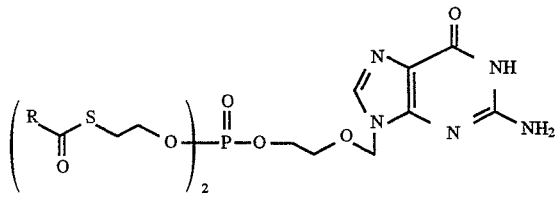

where $R=CH_3$ or $(CH_3)_3C$.

6. A pharmaceutical composition comprising the compound of claim 1 as an active ingredient and a pharmaceutically acceptable diluent, carrier or excipient.

7. The pharmaceutical composition according to claim 6 exhibiting inhibitory activity against a virus whose thymidine kinase activity is either reduced or missing.

8. The pharmaceutical composition according to claim 6 exhibiting inhibitory activity against HIV virus, Hepatitis B virus, Herpes virus type 1 or 2, or cytomegalovirus.

9. A pharmaceutical composition comprising a compound of claim 5 as an active ingredient and a pharmaceutically acceptable excipient diluent or carrier.

10. The antiviral pharmaceutical composition according to claim 9 exhibiting inhibitory activity against Hepatitis B virus, a virus whose thymidine kinase activity is either reduced or missing, HIV virus, Herpes viruses types 1 or 2, or cytomegalovirus.

11. The compound of claim 1 where n is 1 or 2.

12. The compound of claim 1 wherein X is —C(=Z)—Y and Y is $CH_3$ or $(CH_3)_3$—C.

13. The compound of claim 12 wherein R is $(CH_2)_n$—S—C(=O)—$CH_3$ or $(CH_2)_n$—S—C(=O)—tBu, and n is 1 or 2.

14. The compound of claim 1 wherein Y and U are alkyl which is optionally substituted with OH, SH or $NH_2$.

* * * * *

UNITED STATES PATENT AND TRADEMARK OFFICE
CERTIFICATE OF CORRECTION

PATENT NO.   : 5,627,185
DATED        : May 6, 1997
INVENTOR(S)  : Gosselin et al.

It is certified that error appears in the above-identified patent and that said Letters Patent is hereby corrected as shown below:

<u>Column 7,</u>
Line 13, please delete "(s,6H, $CH_2COS$)" and insert therefor -- (s, 6H, $CH_3COS$) --.

Signed and Sealed this

Twenty fifth Day of September, 2001

*Attest:*

NICHOLAS P. GODICI
*Attesting Officer*   *Acting Director of the United States Patent and Trademark Office*